(12) United States Patent
Liu

(10) Patent No.: US 11,452,886 B2
(45) Date of Patent: Sep. 27, 2022

(54) RADIOTHERAPY EQUIPMENT

(71) Applicants: OUR UNITED CORPORATION, Xi'an (CN); Shenzhen OUR New Medical Technologies Development Co., Ltd., Shenzhen (CN)

(72) Inventor: Haifeng Liu, Xi'an (CN)

(73) Assignees: OUR UNITED CORPORATION, Xi'an (CN); Shenzhen OUR New Medical Technologies Development Co., Ltd., Shenzhen (CN)

( * ) Notice: Subject to any disclaimer, the term of this patent is extended or adjusted under 35 U.S.C. 154(b) by 51 days.

(21) Appl. No.: 16/928,440

(22) Filed: Jul. 14, 2020

(65) Prior Publication Data

US 2020/0338368 A1     Oct. 29, 2020

Related U.S. Application Data

(63) Continuation of application No. PCT/CN2019/070274, filed on Jan. 3, 2019.

(30) Foreign Application Priority Data

Jan. 15, 2018   (CN) .......................... 201810036767.8

(51) Int. Cl.
*A61N 5/10* (2006.01)

(52) U.S. Cl.
CPC ......... *A61N 5/1082* (2013.01); *A61N 5/1065* (2013.01); *A61N 2005/1092* (2013.01)

(58) Field of Classification Search
None
See application file for complete search history.

(56) References Cited

U.S. PATENT DOCUMENTS

| | | | | |
|---|---|---|---|---|
| 8,139,714 | B1 * | 3/2012 | Sahadevan | A61N 5/025 378/65 |
| 8,173,983 | B1 * | 5/2012 | Sahadevan | A61N 5/1084 250/341.7 |
| 9,694,210 | B2 * | 7/2017 | Liu | A61B 6/486 |
| 2007/0025513 | A1 * | 2/2007 | Ghelmansarai | G01T 1/2018 378/98.8 |

FOREIGN PATENT DOCUMENTS

| | | |
|---|---|---|
| CN | 101927064 | 12/2010 |
| CN | 108175955 | 6/2018 |
| CN | 208493021 | 2/2019 |
| WO | 2015062093 | 5/2015 |

* cited by examiner

*Primary Examiner* — Hoon K Song
(74) *Attorney, Agent, or Firm* — Emerson, Thomson & Bennett, LLC; Roger D. Emerson; Warren A. Rosborough

(57) ABSTRACT

A radiotherapy equipment is provided. The radiotherapy equipment comprises at least two radiation apparatuses, the radiation apparatuses are configured to be capable of emitting radiation beams, the radiation beams emitted by at least two of the radiation apparatuses intersect at an intersection point, the radiation apparatuses are rotatable circumferentially about a rotation axis, and radiation positions of at least two of the radiation apparatuses are positioned at different cross-sections with respect to the rotation axis.

17 Claims, 10 Drawing Sheets

RADIOTHERAPY EQUIPMENT

CROSS-REFERENCE TO RELATED APPLICATION

This application is a continuation of International Application No. PCT/CN2019/070274 filed on Jan. 3, 2019 and entitled "RADIOTHERAPY EQUIPMENT AND RADIOTHERAPY SYSTEM". The International Application claims priority to Chinese Patent Application No. 201810036767.8, filed on Jan. 15, 2018 and entitled "RADIOTHERAPY EQUIPMENT". The entire disclosures of the prior applications are hereby incorporated by reference in their entirety.

TECHNICAL FIELD

The present disclosure relates to the technical field of medical instruments, in particular to a radiotherapy equipment.

BACKGROUND

Radiotherapy is one of the three major methods for treating tumors. About 65-70% of cancer patients receive radiotherapy to varying degrees.

An existing common radiotherapy equipment is shown in FIG. 1(a). The radiotherapy equipment includes a rotatable gantry, a treatment head arranged on the gantry, and a treatment couch. As shown in FIG. 1(b), the gantry with the treatment head 2 rotates along a rotation axis of the gantry to form a rotating plane of the treatment head, and the treatment couch rotates about a rotation axis of the treatment couch to form a rotating plane of the treatment couch, thereby achieving non-coplanar rotation focusing by means of rotation of the treatment couch and the treatment head, reducing the radio of therapy and radiation doses, and maximizing the protection of normal tissues and cells of the human body while killing cancer cells with radiation beams.

FIGS. 2(a) and 2(b) are schematic diagrams of another radiotherapy equipment, including a drum, a treatment head arranged on the drum, and a treatment couch. Referring to FIG. 2(b), the drum is rotatable about an axis of the drum, and the treatment head moves along an arc-shaped guide rail with respect to the axis of the drum, thereby achieving non-coplanar rotation focusing by means of circumferential rotation of the treatment head and axis movement of the drum.

Therapists found in use of the existing radiotherapy equipment that, when the treatment couch and the treatment head rotate simultaneously, the treatment couch and the treatment head are likely to collide. In addition, the confirmation of a non-coplanar angle completely relies on the subjective judgment of a therapist, and the therapist confirms different non-coplanar angles according to different patients or different contours of bodies, so that the design of a treatment plan is relatively difficult and the treatment period is long.

SUMMARY

The embodiments of the present disclosure provide a radiotherapy equipment, which solves the problems that an existing radiotherapy equipment is prone to collision when implementing non-coplanar focusing treatment or a treatment plan is relatively difficult to design, and the treatment period is long.

In order to solve the above technical problems, the embodiments of the present disclosure adopt the following technical solutions.

A radiotherapy equipment includes at least two radiation apparatuses, the radiation apparatuses are configured to be capable of emitting radiation beams, the radiation beams emitted by at least two of the radiation apparatuses intersect at an intersection point, the radiation apparatuses are rotatable circumferentially about a rotation axis, and radiation positions of at least two of the radiation apparatuses are positioned at different cross-sections with respect to the rotation axis.

A radiotherapy equipment includes at least two radiation apparatuses, radiation beams emitted by at least two of the radiation apparatuses intersect at a target region, the radiation apparatuses are rotatable circumferentially about a rotation axis, and at least two of the radiation apparatuses are positioned at different axial positions with respect to the rotation axis.

A radiotherapy equipment includes at least two radiation apparatuses, radiation beams emitted by at least two of the radiation apparatuses intersect at a target region, and at least two of the radiation apparatuses are positioned at different axial positions with respect to the rotation axis.

A radiotherapy equipment provided by an embodiment of the present disclosure includes at least two radiation apparatuses, the radiation apparatuses are configured to be capable of emitting radiation beams, the radiation beams emitted by at least two of the radiation apparatuses intersect at an intersection point, the radiation apparatuses are rotatable circumferentially about a rotation axis, radiation positions of at least two of the radiation apparatuses are positioned at different cross-sections, then the radiation beam emitted by each of the radiation apparatus respectively forms a rotating plane, and the radiation beam rotating planes of the radiation apparatuses do not coincide, thereby achieving non-coplanar rotation focusing treatment of radiotherapy, reducing the radio of therapy and radiation doses, and maximizing the protection of normal tissues and cells of the human body while killing cancer cells with the radiation beams. In addition, the radiotherapy equipment according to the embodiment of the present disclosure achieves non-coplanar irradiation without a treatment couch, so the problem of collision between the radiation apparatuses and the treatment couch can be avoided.

BRIEF DESCRIPTION OF THE DRAWINGS

In order to describe the technical solution in embodiments of the present disclosure or the prior art more clearly, the drawings which need to be used in the description of the embodiments or the prior art will be simply introduced below. Obviously, the accompanying drawings in the following description show merely some embodiments of the present disclosure, and those of ordinary skill in the art may still derive other drawings according to these drawings without creative efforts.

REFERENCE SIGNS

10—radiotherapy equipment; 11, 11a, 11b, 11c—radiation apparatus; 12—drum; 13—treatment head; 14—collimator; 141—radiation beam channel; 142—diaphragm plate; 15—guide rail.

DETAILED DESCRIPTION

The technical solution of the present disclosure will be further described in detail below with reference to specific embodiments. Obviously, the described embodiments are merely a part of the embodiments of the present disclosure, rather than all the embodiments. All other embodiments obtained by a person of ordinary skill in the art based on the embodiments of the present disclosure shall fall within the protection scope of the present disclosure.

An embodiment of the present disclosure provides a radiotherapy equipment including at least two radiation apparatuses, the radiation apparatuses are configured to be capable of emitting radiation beams, the radiation beams emitted by at least two of the radiation apparatuses intersect at an intersection point, the radiation apparatuses are rotatable circumferentially about a rotation axis, and radiation positions of the at least two of the radiation apparatuses are positioned at different cross-sections with respect to the rotation axis.

Figure 3:
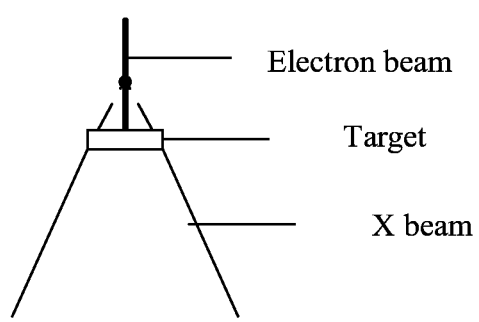
FIG. 3 is a schematic diagram of a virtual radiation position of a radiation apparatus according to an embodiment of the present disclosure.
Figure 16:
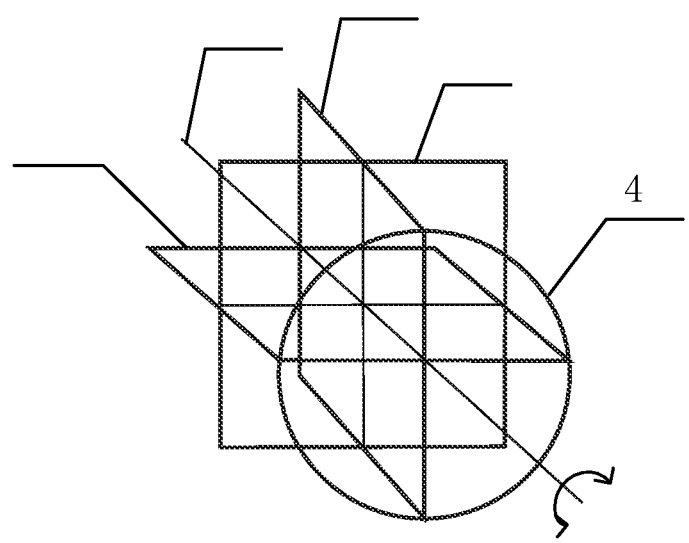
FIG. 16 is a schematic diagram of a three-dimensional plane according to an embodiment of the present disclosure.

It should be noted that, in the embodiment of the present disclosure, a ray source of the radiation apparatus may be an isotope radiation source, such as cobalt-60, then the radiation position of the radiation apparatus may be the isotope radioactive source, and the radiation beam emitted by the radiation apparatus may be a γ beam. Alternatively, the radiation apparatus may be an accelerator, and the accelerator generates an electron beam that hits a target to emit an X beam. In the embodiment of the present disclosure, when the radiation apparatus is an accelerator, the radiation position of the radiation apparatus may be a virtual radiation position as shown in FIG. 3, that is, an intersection point of reverse extension lines of X beams. As shown in FIG. 16, the radiation apparatus rotates about a rotation axis 1 to form a rotating plane 4, and planes 2, 3, and 5 are three planes perpendicular to each other, which are used to illustrate the relationship among the three-dimensional planes in FIG. 4 to facilitate understanding of the embodiments of the present disclosure. In some embodiments of the present disclosure, the cross-section is the plane 3, which is parallel to the rotating plane 4. Due to different positions of different radiation apparatuses, the plurality of rotating planes formed are parallel.

Figure 1A:
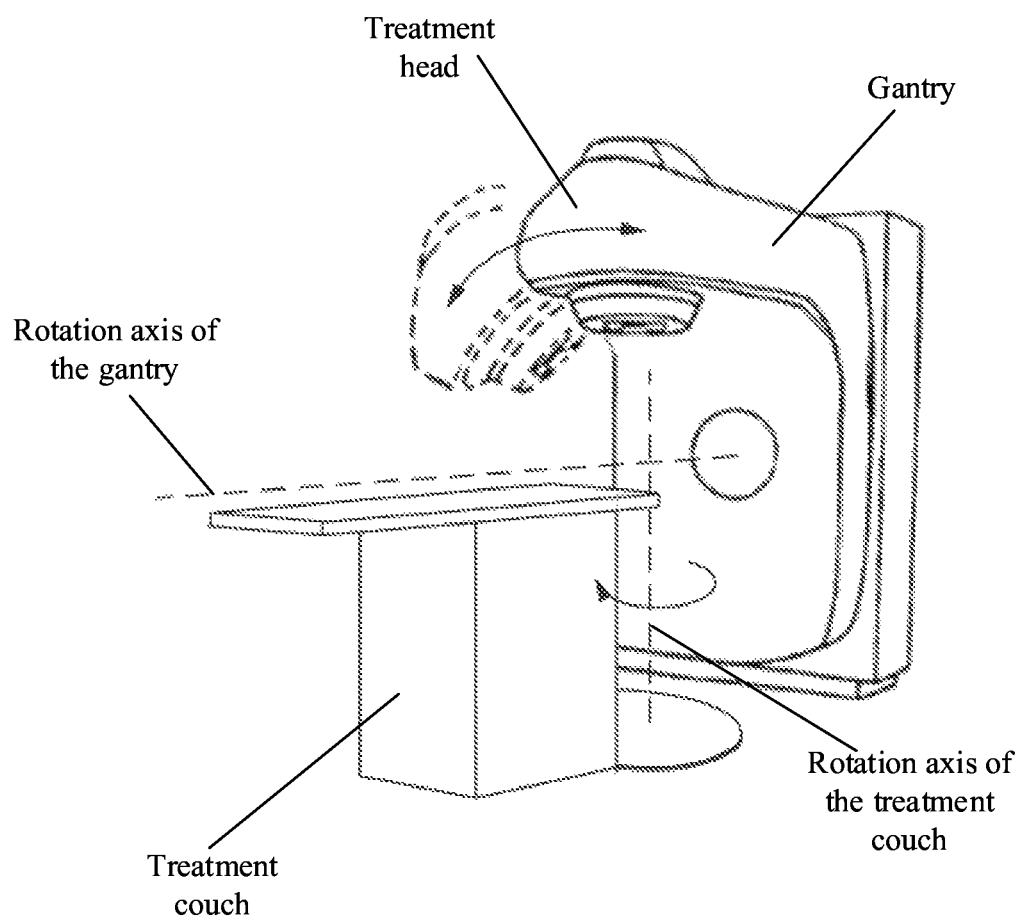
FIG. 1(a) is a schematic diagram of an existing radiotherapy equipment according to the present disclosure.
Figure 1B:
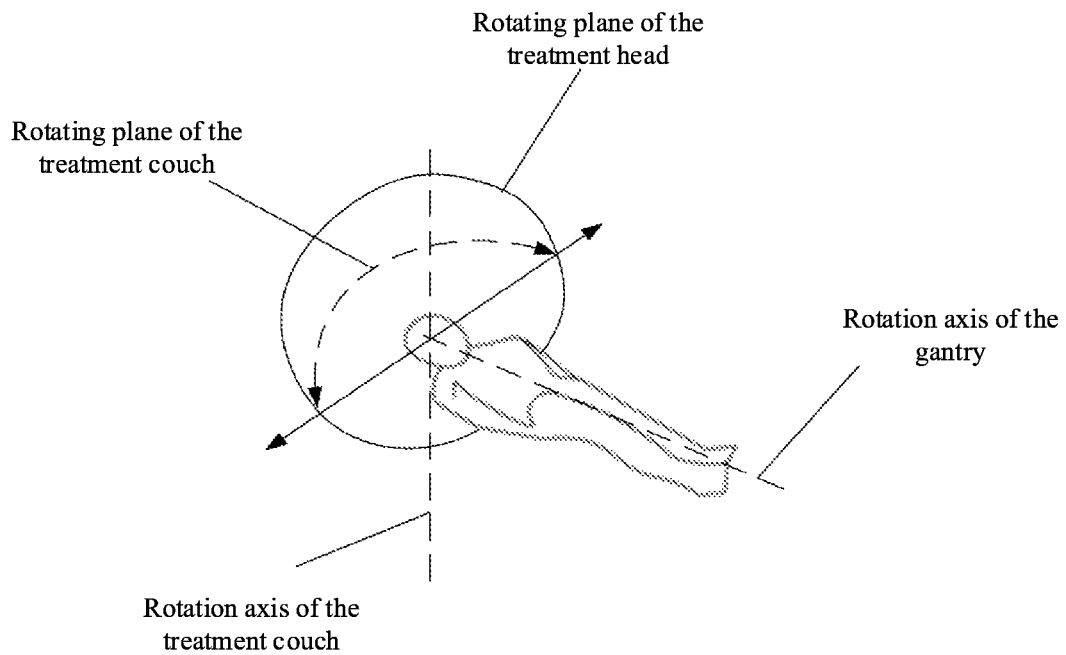
FIG. 1(b) is a schematic diagram of non-coplanar irradiation implemented by the radiotherapy equipment shown in FIG. 1(a)
Figure 2A:
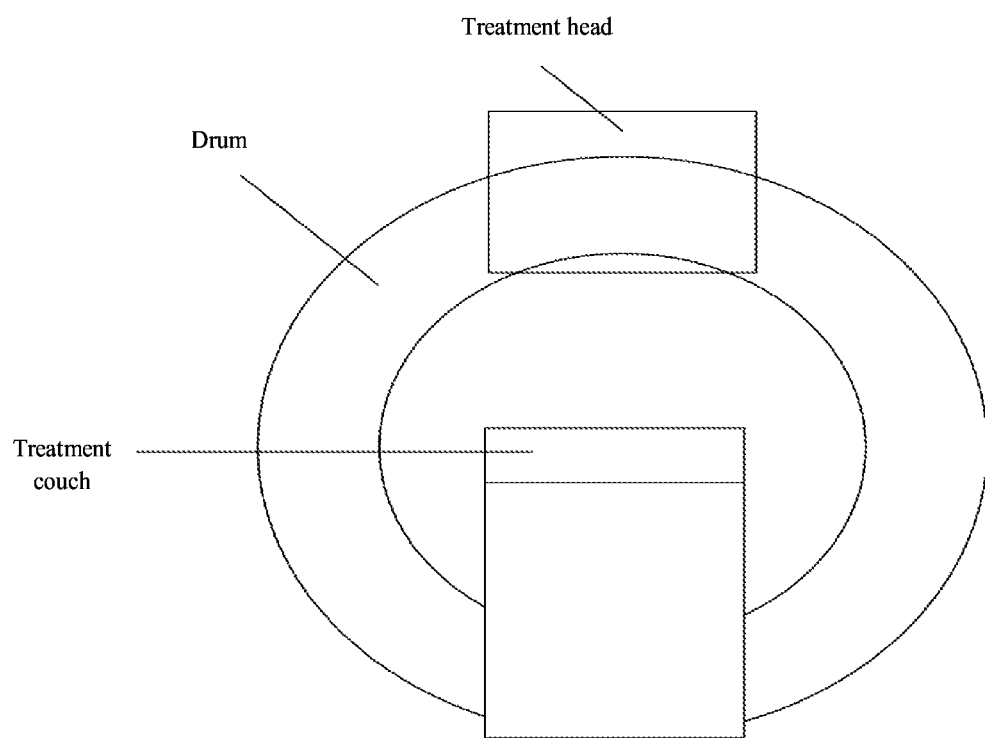
FIG. 2(a) is a schematic diagram of another existing radiotherapy equipment according to the present disclosure.
Figure 2B:
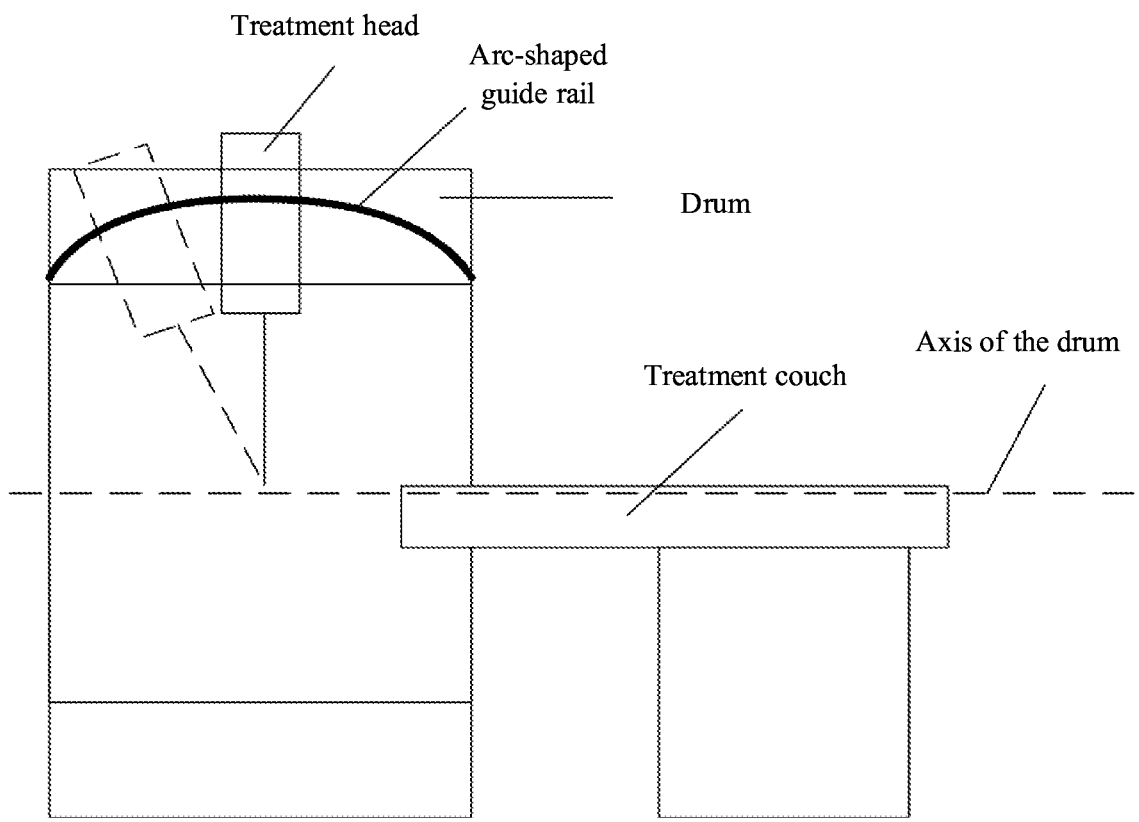
FIG. 2(b) is a schematic diagram of non-coplanar irradiation implemented by the radiotherapy equipment shown in FIG. 2(a)
Figure 4:
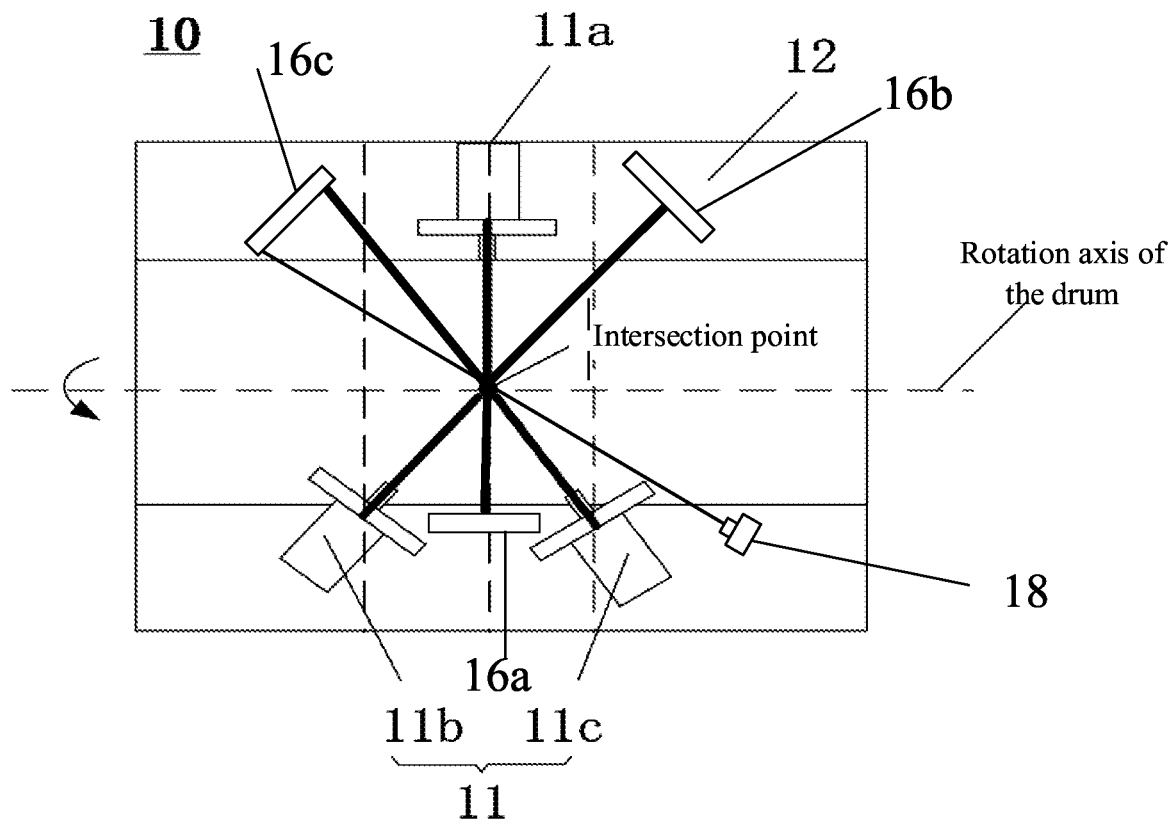
FIG. 4 is a schematic side view of a radiotherapy equipment according to an embodiment of the present disclosure.

The circumferential rotation of the radiation apparatus about the rotation axis may be reciprocating rotation or 360° continuous rotation of the radiation apparatus about the rotation axis. The rotation of the radiation apparatus about the rotation axis may be achieved by mounting the radiation apparatus on a gantry or a manipulator. The gantry may be a C-shaped gantry (see FIG. 1), or a ring gantry (see FIG. 2(a) and FIG. 2(b)). Alternatively, the rotation of the radiation apparatus about the rotation axis may be as shown in FIG. 4, the radiotherapy equipment includes a drum (a type of ring gantry), and the radiation apparatuses are fixed on the drum and rotate circumferentially about an axis of the drum through the drum. Moreover, in the embodiment of the present disclosure, the radiation apparatuses are rotatable about the rotation axis, each radiation apparatus is rotatable about the rotation axis through a rotating device, or a plurality of radiation apparatuses are rotatable about the rotation axis through the same rotating device, or all the radiation apparatuses are rotatable about the rotation axis through a rotating device, which is not limited in the embodiments of the present disclosure.

An embodiment of the present disclosure provides a radiotherapy equipment. The radiotherapy equipment includes a drum, a plurality of radiation apparatuses are arranged on the drum, and the drum drives the plurality of radiation apparatuses to rotate about an axis of the drum as an example. Exemplarily, as shown in FIG. 4, in the embodiment of the present disclosure, the radiotherapy equipment 10 includes a drum 12 and three radiation apparatuses arranged on the drum 12, respectively a radiation apparatus 11a, a radiation apparatus 11b, and a radiation apparatus 11c. Radiation positions of the radiation apparatus 11a, the radiation apparatus 11b, and the radiation apparatus 11c are respectively positioned at three different cross-sections (i.e., three dotted lines shown in FIG. 4), and the radiation apparatuses emit radiation beams that intersect at an intersection point. Taking the intersection point on the rotation axis of the drum as an example, the radiation apparatus 11a, the radiation apparatus 11b, and the radiation apparatus 11c are driven by the drum 12 to rotate along the rotation axis of the drum.

Figure 5:
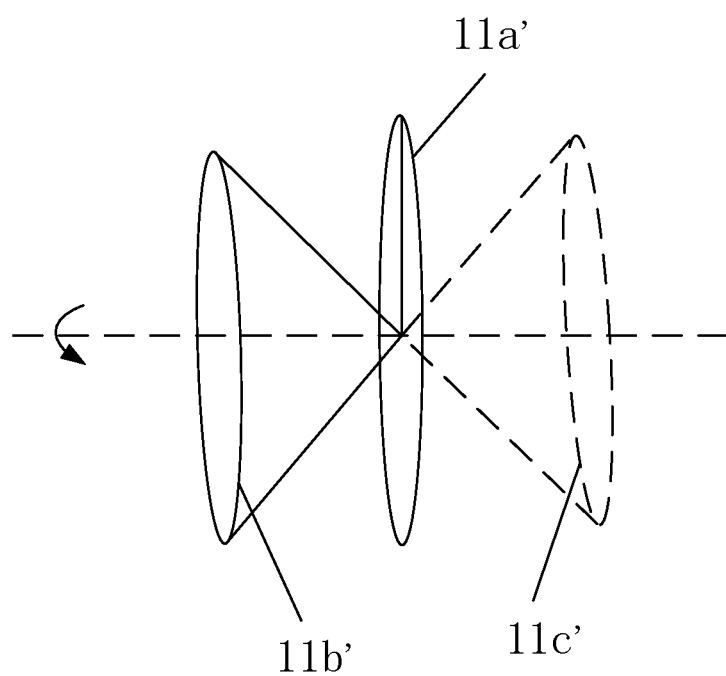
FIG. 5 is a schematic diagram of radiation beam rotating planes of radiation apparatuses of the radiotherapy equipment shown in FIG. 4.

In the embodiment of the present disclosure, if the radiation positions of the radiation apparatuses are positioned at different cross-sections, the radiation apparatuses rotate circumferentially about the rotation axis to form rotating planes. Referring to FIG. 5 for an example, the radiation apparatus 11a rotates about the rotation axis of the drum to form a radiation beam rotating plane 11a', the radiation apparatus 11b rotates about the rotation axis of the drum to form a radiation beam rotating plane 11b' (solid cone plane shown in FIG. 5), and the radiation apparatus 11c rotates about the rotation axis of the drum to form a radiation beam rotating plane 11c' (dotted cone plane shown in FIG. 5). As shown in FIGS. 4 and 5, since the radiation positions of the radiation apparatuses are positioned at different cross-sections, the rotating planes of the three radiation beams do not coincide with each other, that is, the radiation beams of the radiation apparatuses are of non-coplanar irradiation, so that rotating non-coplanar radiotherapy can be achieved without moving the radiation apparatuses or a treatment couch.

Figure 6:
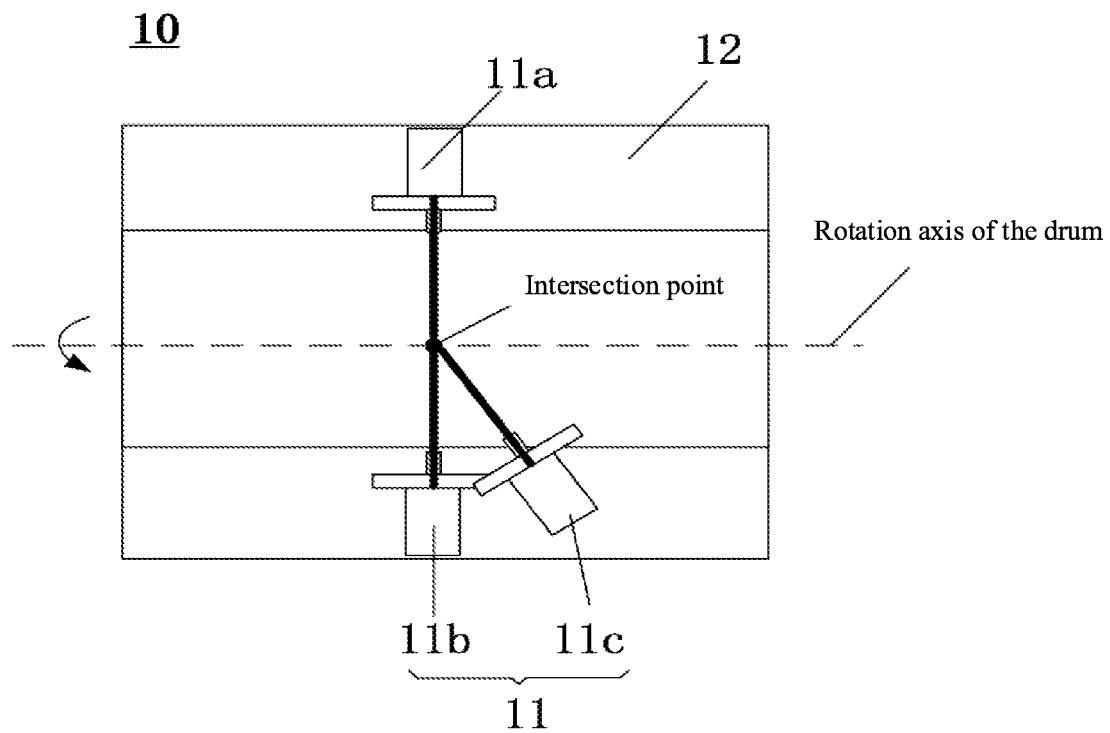
FIG. 6 is a schematic side view of another radiotherapy equipment according to an embodiment of the present disclosure.

It should be noted that in the embodiment of the present disclosure, if each radiation apparatus rotates about the rotation axis to form a radiation beam rotating plane, and the radiation positions of the radiation apparatuses are positioned at different cross-sections, the radiation beam rotating planes of the radiation apparatuses do not coincide. Taking the radiation positions of the three radiation apparatuses being positioned at different cross-sections shown in FIG. 4 as an example, the radiation beam rotating planes formed by the three radiation apparatuses do not coincide as shown in FIG. 5. Exemplarily, the radiation beam rotating planes of the radiation apparatuses may also do not coincide as shown in FIG. 6, then the radiation positions of the radiation apparatus 11a and the radiation apparatus 11b are positioned at the same cross-section and the radiation beam rotating plane formed by the rotation of the radiation apparatus 11a about the rotation axis of the drum coincides with the radiation beam rotating plane formed by the rotation of the radiation apparatus 11b about the rotation axis of the drum. The radiation apparatus 11c is not positioned at the same cross-section as the two radiation apparatuses, and the radiation beam rotating plane formed by the rotation of the radiation apparatus 11c about the rotation axis of the drum does not coincide with the radiation beam rotating planes formed by the rotation of the other two radiation apparatuses about the rotation axis of the drum.

In the embodiment of the present disclosure, the radiation beams emitted by the radiation apparatuses intersect at an intersection point, and the intersection point may or may not be on the rotation axis. If the intersection point is not on the rotation axis, the treatment can be achieved by cooperation of the treatment couch. In the embodiment of the present disclosure, as shown in FIGS. 4 and 6, the intersection point is on the rotation axis as an example for illustration.

Figure 7:
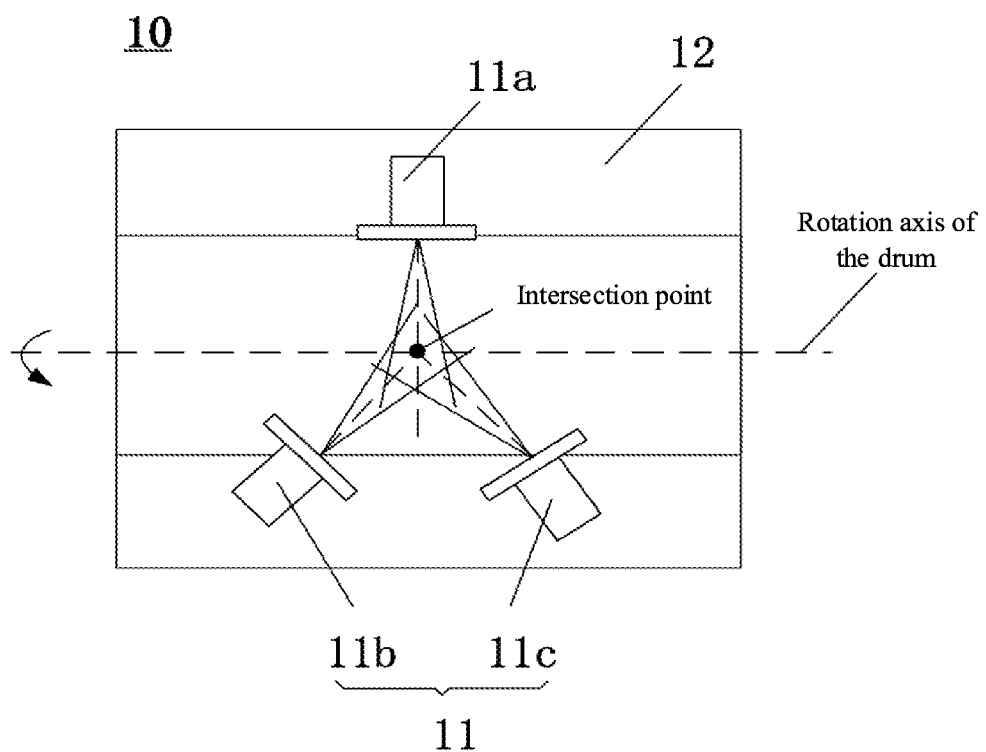
FIG. 7 is a schematic side view of another radiotherapy equipment according to an embodiment of the present disclosure.

In a radiotherapy equipment provided by an embodiment of the present disclosure, the radiation beam emitted by the radiation apparatus is a single beam, as shown in FIG. 4. Of course, the single beam may be shaped into a cone beam, as shown in FIG. 7.

In the embodiment of the present disclosure, when the radiation beam is a cone beam, the radiation beam rotating plane formed by the rotation of the radiation apparatus about the rotation axis is a radiation beam rotating plane formed by the rotation of the axis of the radiation beam emitted by the radiation apparatus. Exemplarily, as shown in FIG. 7, the radiation apparatus 11a, the radiation apparatus 11b, and the radiation apparatus 11c respectively emit cone beams, and the axes of the cone beams form radiation beam rotating planes as shown in FIG. 5.

In the embodiment of the present disclosure, the radiotherapy equipment includes at least two radiation apparatuses, each radiation apparatus is capable of emitting a radiation beam, and the radiation beams emitted by the radiation apparatuses intersect at an intersection point. As shown in FIGS. 4-7, the radiotherapy equipment includes three radiation apparatuses, and the radiation beams emitted by the three radiation apparatuses intersect at an intersection point. Alternatively, the radiotherapy equipment includes four radiation apparatuses, the radiation beams emitted by two of the radiation apparatuses intersect at an intersection point, and the radiation beams emitted by the other two radiation apparatuses intersect at another intersection point. The embodiment of the present disclosure does not limit the number of radiation apparatuses and the positions of intersection points.

A radiotherapy equipment provided by an embodiment of the present disclosure includes at least two radiation apparatuses, the radiation apparatuses are configured to be capable of emitting radiation beams, the radiation beams emitted by the radiation apparatuses intersect at an intersection point, the radiation apparatuses are rotatable circumferentially about a rotation axis, radiation positions of the radiation apparatuses are positioned at different cross-sections, then the radiation beam emitted by each radiation apparatus respectively forms a rotating plane, and the radiation beam rotating planes of the radiation apparatuses do not coincide, thereby achieving non-coplanar rotation focusing treatment of radiotherapy, reducing the radio of therapy and radiation doses, and maximizing the protection of normal tissues and cells of the human body while killing cancer cells with the radiation beams. In addition, the radiotherapy equipment according to the embodiment of the present disclosure achieves non-coplanar irradiation without a treatment couch, so the problem of collision between the radiation apparatus and the treatment couch can be avoided. Moreover, in the embodiment of the present disclosure, the radiation beam rotating planes of the radiation apparatuses do not coincide to achieve non-coplanar rotation focusing, without setting by a therapist, thereby reducing the treatment period and improving the treatment efficiency.

Furthermore, a radiotherapy equipment provided by an embodiment of the present disclosure includes a plurality of radiation apparatuses, and the radiation beams of the radiation apparatuses intersect at an intersection point, which is similar to the principle of magnifying glass focusing, so that the dose rate at the intersection point increases significantly, and the requirement of radiotherapy for high dose rate at the intersection point can be met. Taking the existing accelerator as an example, the X-ray emitted by a radiation apparatus is about 1400 Mu, and the dose rate is about 3.5 Gr. If the radiotherapy equipment includes three radiation apparatuses, the dose rate at the intersection point may reach 10.5 Gr. The dose rate at the intersection point can meet the clinical requirement for high dose rate, so that tumor cells can be killed at a time by single irradiating treatment, and the treatment efficiency is improved.

In a radiotherapy equipment provided by an embodiment of the present disclosure, the radiation position of at least one radiation apparatus is positioned at a cross-section where the intersection point is located. Exemplarily, as shown in FIG. 4, taking the radiation position of a radiation apparatus being positioned at the cross-section where the intersection point is located as an example, the radiation position of the radiation apparatus 11a is positioned at the cross-section where the intersection point is located. Alternatively, the radiation positions of the plurality of radiation apparatuses may be positioned at a cross-section where the intersection point is located. As shown in FIG. 6, the radiation positions of the radiation apparatus 11a and the radiation apparatus 11b are positioned at the cross-section where the intersection point is located. In the case where the radiotherapy equipment includes a plurality of radiation apparatuses, there may be multiple different implementations according to the clinical design, which are not limited in the embodiments of the present disclosure. The present disclosure is illustrated only using the two cases shown in FIGS. 4 and 6 as an example.

Figure 8:
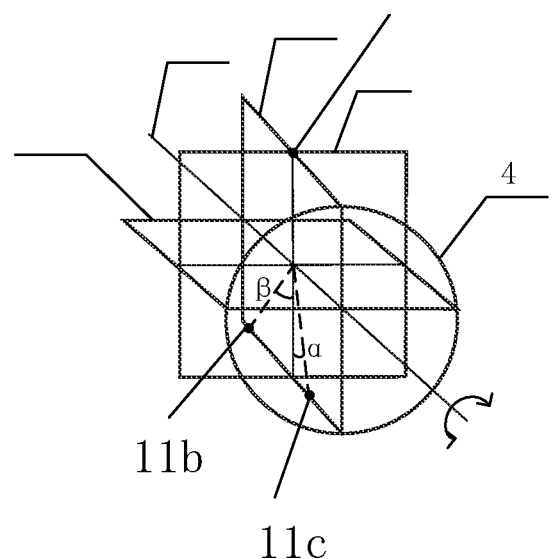
FIG. 8 is a schematic diagram of an angle between a treatment head of the radiotherapy equipment shown in FIG. 4 and a cross-section of an intersection point.

In a radiotherapy equipment provided by an embodiment of the present disclosure, the radiation position of the radiation apparatus is not positioned at a cross-section where the intersection point is located, and the angle between the cross-section where the intersection point is located and the connecting line between the intersection point and the radiation position of the radiation apparatus and the cross-section where the intersection point is located is 0° to 60°. The numerical values in the embodiment of the present disclosure all include a critical value, which may be 0° or 60°. Of course, the angle may also be 10°, 15°, 25°, or 30°, etc., which may be different according to different clinical needs. Exemplarily, as shown in FIG. 8, taking the radiotherapy equipment shown in FIG. 4 as an example, the radiation position of the radiation apparatus 11a is positioned at a cross-section 3 where the intersection point is located, the angle between the connecting line passing through the intersection point and the radiation position of the radiation apparatus 11b and the cross-section 3 of the intersection point is β, and the angle between the connecting line passing through the intersection point and the radiation position of the radiation apparatus 11c and the cross-section 3 of the intersection point is α. Exemplarily, the angles of α and β may be the same or different.

Figure 9:
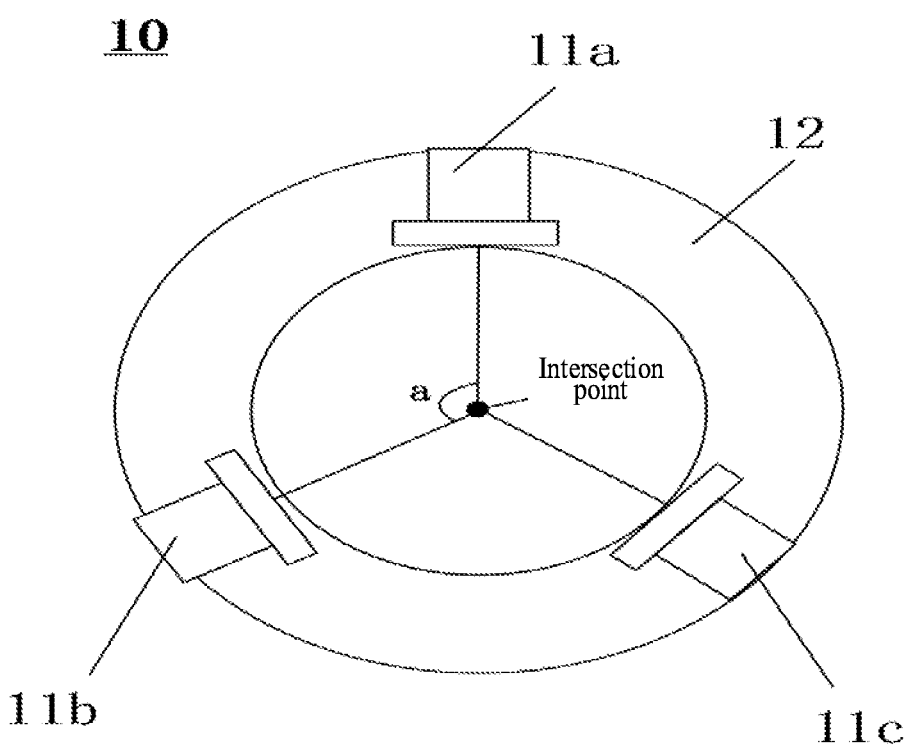
FIG. 9 is a front view of a radiotherapy equipment according to an embodiment of the present disclosure.

In a radiotherapy equipment provided by an embodiment of the present disclosure, projections of radiation apparatuses on the cross-section are distributed circumferentially, and the angle between the projections of two adjacent radiation apparatuses on the cross-section to the intersection point is 0° to 180°. Exemplarily, as shown in FIG. 9, the radiotherapy equipment includes a drum 12, and a radiation apparatus 11a, a radiation apparatus 11b and a radiation apparatus 11c arranged on the drum 12. The drum drives each radiation apparatus to rotate about a rotation axis of the drum, and focal points of the three radiation apparatuses are on the rotation axis of the drum. In FIG. 9, the angle between the projections of the radiation apparatus 11a and the radiation apparatus 11b on the cross-section is a as an example, and the angle a is exemplified as 120°. Of course, in the embodiment of the present disclosure, the angle between the projections of any two of the radiation apparatuses on the cross-section is 0 to 180°. For example, as shown in FIG. 9, the angle between the projections of the radiation apparatus 11a and the radiation apparatus 11c on the cross-section, and the angle between the projections of the radiation apparatus 11b and the radiation apparatus 11c on the cross-section, may be 120°. The embodiment of the present disclosure does not limit the angle between the projections of the radiation apparatuses on the cross-section, only taking FIG. 9 as an example for illustration.

In a radiotherapy equipment provided by an embodiment of the present disclosure, each radiation apparatus is provided with a rotating device, and the rotating device drives the radiation apparatus to rotate circumferentially about a rotation axis. Exemplarily, each radiation apparatus is driven by a manipulator to rotate circumferentially about the rotation axis. Alternatively, the radiation apparatuses are arranged on a rotating device, and the rotating device drives the radiation apparatuses to rotate circumferentially about the rotation axis. As shown in FIGS. 4 and 6, three radiation apparatuses are arranged on a ring gantry, and the ring gantry drives them to rotate circumferentially about the rotation axis of the drum. Of course, the driving device may also be a device besides the manipulator or the gantry, which is not limited in the embodiment of the present disclosure.

In the radiotherapy equipment provided by the embodiment of the present disclosure, when the gantry is a ring gantry, a plurality of radiation apparatuses are arranged on the ring gantry, and the ring gantry drives the plurality of radiation apparatuses to rotate about the axis of the ring gantry, or, the radiation apparatuses are rotatable circumferentially on the ring gantry along the axis of the ring gantry.

In a radiotherapy equipment provided by an embodiment of the present disclosure, the radiation apparatus may swing and/or move relative to the manipulator or the gantry. An example of swinging may be implemented by a universal wheel or the like, and the radiation apparatus may not change in position, but the swinging changes the direction of the radiation beam of the radiation apparatus. The movement may be implemented by a guide rail or a gear ring, etc., which is not limited in the embodiment of the present disclosure. The radiation apparatus may swing and/or move relative to the manipulator or gantry, that is, the radiation apparatus may swing relative to the manipulator or gantry, or the radiation apparatus may move relative to the manipulator or gantry, or the radiation apparatus may swing and move relative to the manipulator or gantry.

Figure 10:
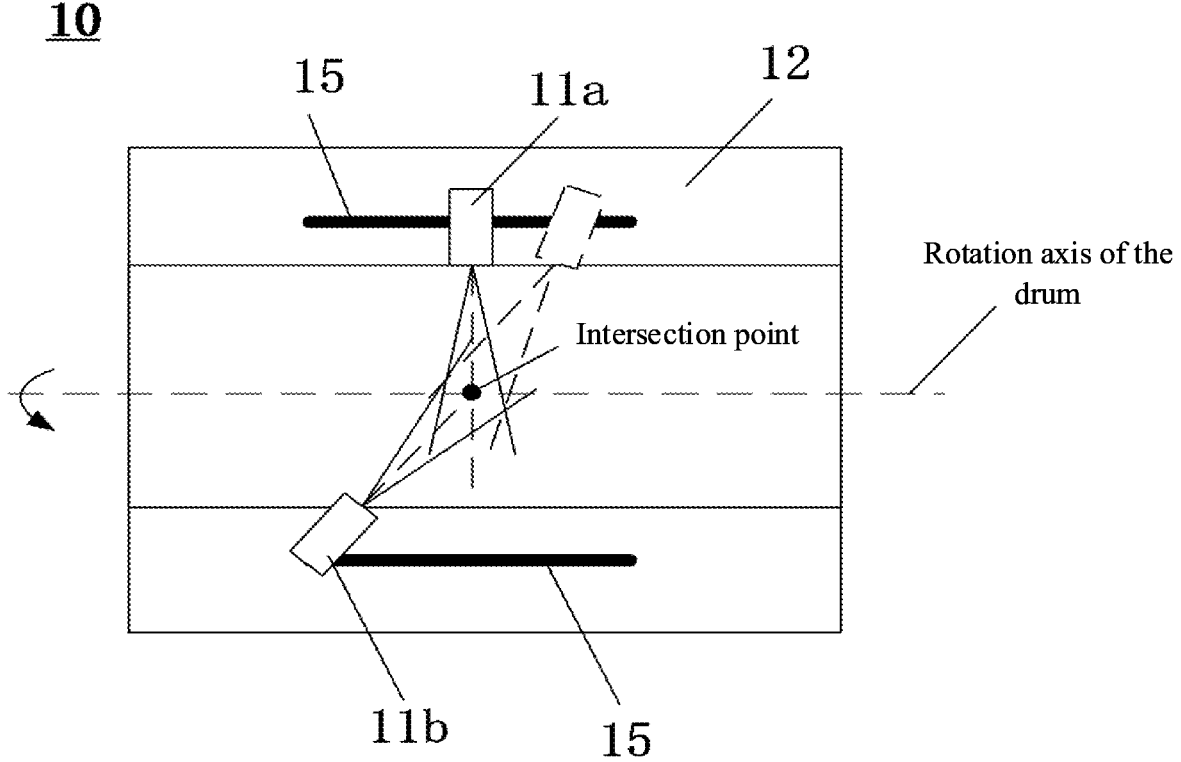
FIG. 10 is a schematic side view of another radiotherapy equipment according to an embodiment of the present disclosure.

For example, the radiation apparatus may swing and/or move relative to the manipulator or gantry axially along the rotation axis. As shown in FIG. 10, the radiotherapy equipment includes two radiation apparatuses as an example, the radiotherapy equipment further includes guide rails 15, each radiation apparatus is provided with a guide rail 15, and the radiation apparatus 11a and the radiation apparatus 11b may move along the guide rails 15 respectively. Taking the movement of the radiation apparatus 11a along the guide rail 15 as an example in FIG. 10, the positions of the radiation apparatus 11a intersecting at the intersection point before and after moving are unchanged.

Figure 11:
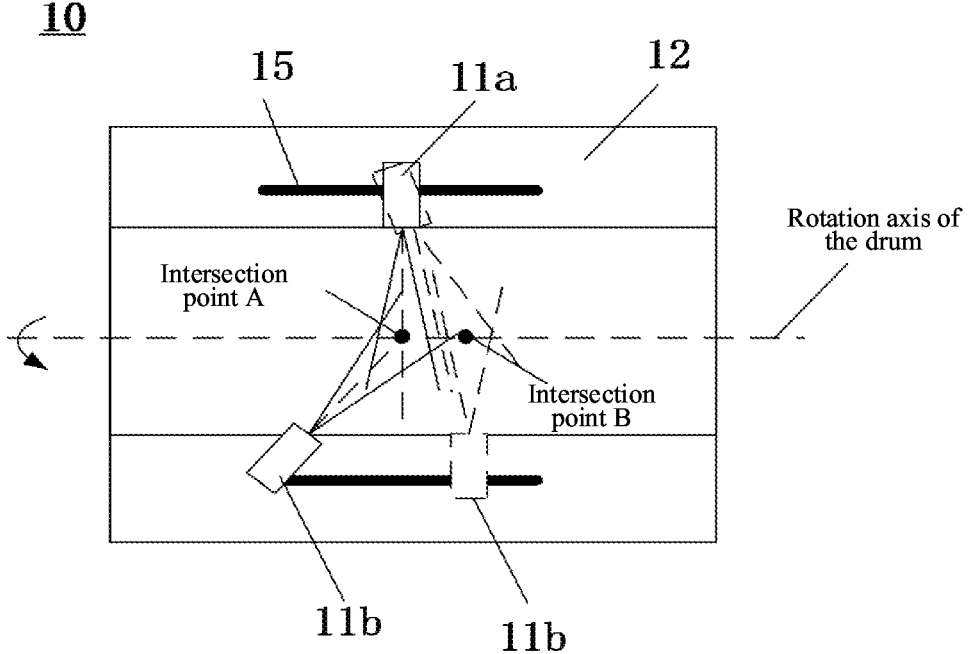
FIG. 11 is a schematic side view of another radiotherapy equipment according to an embodiment of the present disclosure.

In a radiotherapy equipment provided by an embodiment of the present disclosure, as shown in FIG. 10, after the radiation apparatus swings and/or moves relative to the manipulator or the gantry, the position of its intersection point is unchanged. Of course, after the radiation apparatus swings and/or moves relative to the manipulator or the gantry, the position of its intersection point may also be changed. For example, as shown in FIG. 11, the radiotherapy equipment further includes guide rails 15, each radiation apparatus is provided with a guide rail 15, the radiation beams of the radiation apparatus 11a and the radiation apparatus 11b intersect at an intersection point A, and after the radiation apparatus 11a swings and the radiation apparatus 11b moves along the guide rail 15, the radiation beams of the radiation apparatus 11a and the radiation apparatus 11b intersect at an intersection point B, so the movement of the treatment couch can also cooperate with the change of the intersection point for treatment. This application does not limit the swinging and moving positions of the radiation apparatuses relative to the manipulator or gantry and the intersection points, only taking the description shown in FIGS. 10 and 11 as an example.

In a radiotherapy equipment provided by an embodiment of the present disclosure, the plurality of radiation apparatuses are a X-ray generators; or, the plurality of radiation apparatuses are γ-ray devices; or, the radiation apparatuses include X-ray generators and γ-ray devices.

The radiation apparatuses are all X-ray generators. For example, the radiotherapy equipment includes three radiation apparatuses, and all the three radiation apparatuses emit X-rays. The plurality of radiation apparatuses are all γ-ray devices. For example, the radiotherapy equipment includes three radiation apparatuses. Each of the three radiation apparatuses includes a cobalt-60 radiation source, which emits γ-rays. The γ-rays are shaped by a collimator to form a single radiation beam for emission. The radiation apparatuses include X-ray generators and γ-ray devices. For example, the radiotherapy equipment includes three radiation apparatuses, two of which may be X-ray generators and one is a γ-ray device. That is, the radiotherapy equipment can realize the combined application of X-rays and γ-rays. The X-ray generator may be an X-knife, that is, X-rays are shaped by a collimator to form a single beam for emission. The γ-rays emitted by the γ-ray device may also be shaped by a collimator to form a single beam for emission.

If the radiation apparatus emits an X beam, the radiation apparatus may be an X-knife. The X beam is shaped by a collimator to form a radiation beam having a diameter of 2 mm to 60 mm for fill-in focusing irradiation treatment of tumors. Alternatively, the radiotherapy equipment further includes a multi-leaf collimator. When the radiation apparatus emits an X beam, the X beam is shaped by the multi-leaf collimator to form a radiation field similar to the shape of the tumor, so as to achieve conformal intensity modulated radiotherapy.

A radiotherapy equipment provided by an embodiment of the present disclosure includes three radiation apparatuses, all of which are X-ray generators. Each ray generator may form a circular or approximately circular X beam through a collimator, and the X beams of the three radiation apparatuses intersect at an intersection point, and are approximately spherical at the intersection point.

Of course, the radiotherapy equipment may include a plurality of radiation apparatuses, and the radiation apparatuses may be X-ray generators. Each ray generator may form a circular or approximately circular X beam through a collimator, and the X beams of the plurality of radiation apparatuses intersect at an intersection point, and can form more three-dimensional shapes at the intersection point.

Figure 12:
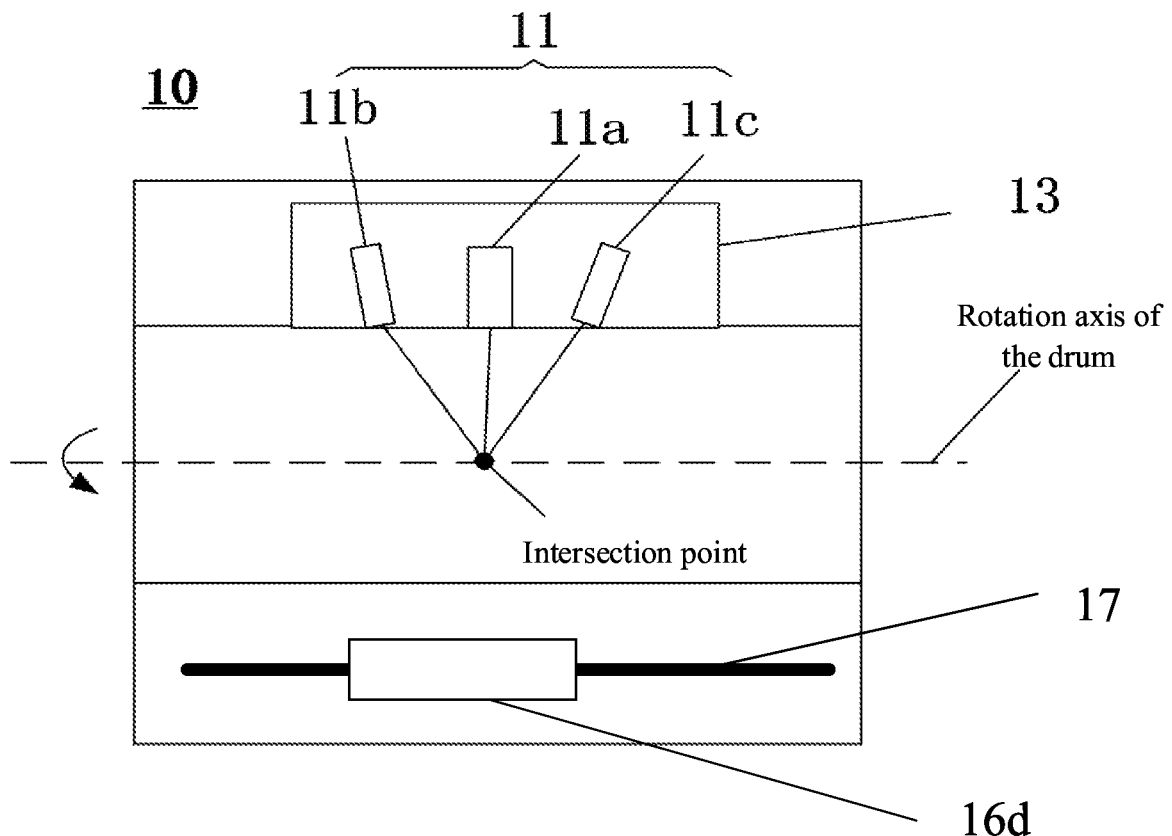
FIG. 12 is a schematic side view of another radiotherapy equipment according to an embodiment of the present disclosure.

In the radiotherapy equipment provided by the embodiment of the present disclosure, the three radiation apparatuses are arranged on a fixing device, the fixing device is fixed on the gantry, and the gantry drives the fixing device to rotate about the axis of the gantry. Exemplarily, as shown in FIG. 12, the three radiation apparatuses, i.e., the radiation apparatus 11*a*, the radiation apparatus 11*b*, and the radiation apparatus 11*c*, are arranged on a fixing device 13. Then, the radiation apparatuses may move circumferentially through the rotation of the fixing device. For example, the gantry of the radiotherapy equipment may be a drum, the fixing device may be fixed on the drum, and the radiation apparatuses are driven by rotation of the drum to rotate about the rotation axis.

In a radiotherapy equipment provided by an embodiment of the present disclosure, the radiation positions of the three radiation apparatuses are positioned at different cross-sections with respect to the rotation axis; or, the radiation positions of two of the radiation apparatuses are positioned at the same cross-section, and the radiation positions of the two of the radiation apparatuses and the radiation position of a third of the radiation apparatuses is at different cross-sections.

Figure 13A:
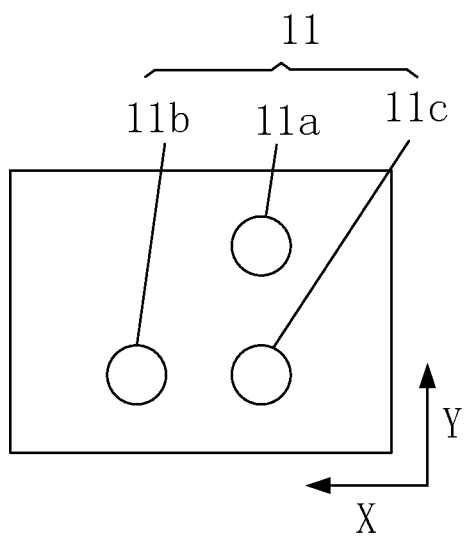
FIG. 13(a) is a schematic top view of a treatment head of the radiotherapy equipment shown in FIG. 12.
Figure 13:
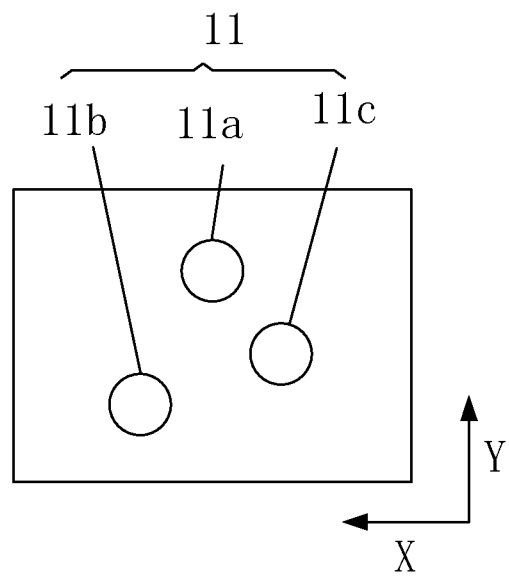
FIG. 13(b) is another schematic top view of the treatment head of the radiotherapy equipment shown in FIG. 12.

The radiation positions of the three radiation apparatuses are positioned at different cross-sections, for example, as shown in FIG. 13(*b*), the radiation positions of the radiation apparatus 11*a*, the radiation apparatus 11*b*, and the radiation apparatus 11*c* are positioned at different cross-sections, and the radiation beam rotating planes of the three radiation apparatuses do not coincide after circumferential rotation.

Alternatively, the radiation beam rotating planes of two of the radiation apparatuses coincide, and do not coincide with the radiation beam rotating plane of the third radiation apparatus. As shown in FIG. 13(*a*), the radiation apparatus 11*b* and the radiation apparatus 11*c* are positioned at the same cross-section, the radiation beam rotating planes of the radiation apparatus 11*b* and the radiation apparatus 11*c* coincide after circumferential rotation, while the radiation apparatus 11*b* and the radiation apparatus 11*a* or the radiation apparatus 11*c* are positioned at different cross-sections, and the radiation beam rotating plane of the radiation apparatus 11*b* does not coincide with the radiation beam rotating plane of the radiation apparatus 11*a* or the radiation apparatus 11*c*.

Of course, the position distribution of the three radiation apparatuses is not limited to that shown in FIGS. 13(*a*) and 13(*b*), and the present disclosure is only exemplified by the two cases shown in FIGS. 13(*a*) and 13(*b*).

An embodiment of the present disclosure provides a radiotherapy equipment. In the case where the radiotherapy equipment includes a plurality of X-ray generators, each of the plurality of X-ray generators is provided with an acceleration module, or the plurality of radiation apparatuses share an acceleration module. Taking the example shown in FIG. 4, the radiotherapy equipment includes three radiation apparatuses. The radiation apparatus 11*a*, the radiation apparatus 11*b*, and the radiation apparatus 11*c* are all X-ray generators. The radiation apparatus 11*a*, the radiation apparatus 11*b*, and the radiation apparatus 11*c* may share an acceleration module, for example, share an electron beam generator, a waveguide, or the like. Alternatively, the radiation apparatus 11*a*, the radiation apparatus 11*b*, and the radiation apparatus 11*c* respectively correspond to an acceleration module. This application does not limit this, and only uses the above as an example for illustration.

In a radiotherapy equipment provided by an embodiment of the present disclosure, each radiation apparatus is provided with a collimator, the collimator provides a radiation beam channel for shaping radiation beams, and the collimators of the plurality of radiation apparatuses are the same or different.

It should be noted that if the radiation apparatus is an X-ray generator, its working principle is that the accelerator accelerates particles to form photons, and the photons hit the target to emit X-rays. Generally, the rays are emitted outward. In order to make the rays meet the clinical treatment requirements, the X-rays are shaped by the collimator. If the radiation apparatus includes a cobalt-60, the cobalt-60 emits a γ beam. In order to make the rays meet the clinical treatment requirements, the γ beam is shaped by the collimator.

Figure 14:
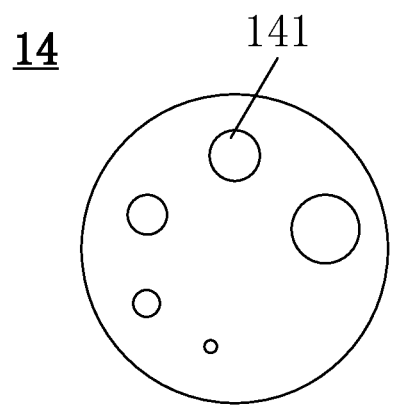
FIGS. 14(a) and 14(b) are schematic diagrams of a collimator according to an embodiment of the present disclosure.
Figure 14:
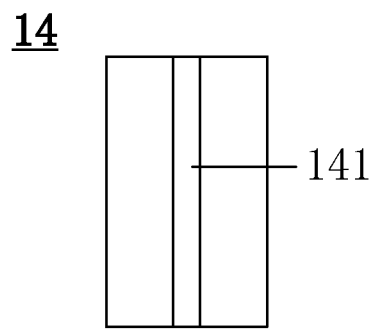
Figure 15:
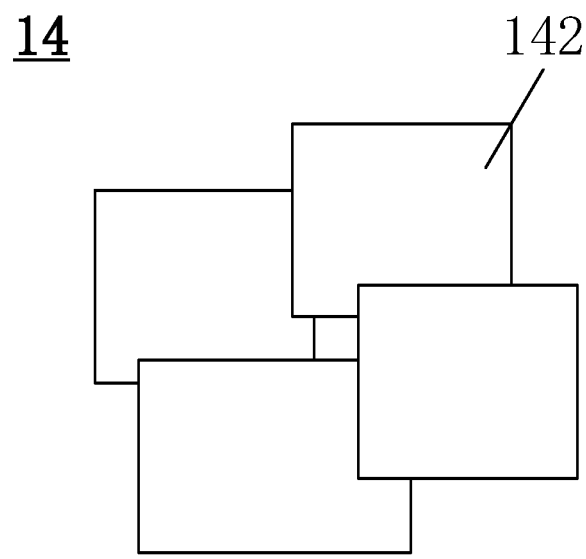
FIG. 15 is a conformal schematic diagram of another collimator according to an embodiment of the present disclosure.

For example, as shown in FIGS. 14(*a*) and 14(*b*), the collimator 14 is provided with a plurality of beam channels 141 having different aperture sizes, which can be used for focusing treatment in a filling manner. The collimator 14 in FIG. 14(*a*) is provided with five beam channels of different apertures as an example, the collimator 14 in FIG. 14(*b*) is provided with one beam channel 141 as an example, and the embodiment of the present disclosure does not limit the size and shape of the specific beam channels. Alternatively, the collimator may shape beam channels of different sizes and/or shapes. For example, the collimator may be a multi-leaf collimator including two groups of opposite leaves, and may shape beam channels of different sizes and/or shapes through the movement of the leaves to achieve conformal irradiation treatment. Of course, as shown in FIG. 15, the collimator 14 may include a plurality of diaphragm plates 142 to shape beam channels of different sizes and/or shapes, and the radiation beams in the radiation beam channels may also achieve focusing treatment by filling. FIG. 15 shows four diaphragm plates as an example for illustration. The embodiment of the present disclosure does not limit the number of diaphragm plates.

In the embodiment of the present disclosure, each of the radiation apparatuses is provided with a collimator, and the collimators of the plurality of radiation apparatuses are the same or different. The collimators of the plurality of radiation apparatuses are the same, for example, the radiotherapy equipment includes three radiation apparatuses, the collimators of the radiation apparatuses are the same, and they may be the collimators shown in FIG. 14(*a*) or 14(*b*), or the collimators shown in FIG. 15, or multi-leaf collimators. The collimators of the plurality of radiation apparatuses are different, for example, the radiotherapy equipment includes three radiation apparatuses, the collimators of two radiation apparatuses may be multi-leaf collimators, and the collimator of the other radiation apparatus may be the collimator shown in FIG. 14(*a*), 14(*b*), or 15. Alternatively, the radiotherapy equipment includes three radiation apparatuses, the collimator of one radiation apparatus may be a multi-leaf collimator, the collimator of the other radiation apparatus may be the collimator shown in FIG. 14(*a*) or 14(*b*), and the collimator of another radiation apparatus may be the collimator shown in FIG. 15. The embodiment of the present disclosure does not limit the types of the plurality of radiation apparatuses and the collimators of the radiation apparatuses, and only take the above as an example for illustration.

The radiotherapy equipment according to an embodiment of the present disclosure further includes an imaging device, and the imaging device includes a beam generator and a beam receiving detector. The imaging device may be arranged on the radiotherapy equipment, or on a ceiling or bottom surface of a radiotherapy room. In the case where the radiotherapy equipment includes a drum, the imaging device may also be arranged on the drum. The radiation beam emitted by the beam generator of the imaging device passes through the intersection point and is received by the beam receiving detector. Further, the imaging device may include two beam generators and two beam receiving detectors, and the radiation beams emitted by the two beam generators intersect.

The radiotherapy equipment according to an embodiment of the present disclosure includes detector panels, for example, as show in FIG. 4, the detector panels 16*a*, 16*b* and 16*c* are respectively arranged on opposite sides of the radiation apparatuses 11*a*, 11*b* and 11*c* and can respectively receive the radiation beams of the radiation apparatuses 11*a*, 11*b* and 11*c* to detect the dosages or field shapes of the radiation beams of the radiation apparatuses 11*a*, 11*b* and 11*c*, so that the parameters of the radiation beams can be confirmed in order to check with a treatment plan to determine the effectiveness of the treatment.

The radiotherapy equipment in the embodiment of the present disclosure includes a plurality of radiation apparatuses, for example, one detector panel 16*d* may receive radiation beams of at least two of the radiation apparatuses, or one detector panel 16*c* may receive radiation beams of a radiation apparatus 11*c* and a beam generator 18, thereby reducing the number of detector panels used, lowering equipment costs, and enlarging the treatment space. For example, as shown in FIG. 12, taking a detector panel 16*d* that can receive radiation beams of the at least two of the radiation apparatuses 11*a*, 11*b* and 11*c* as an example, the detector panel 16*d* may be moved by a manipulator or slid on a slide rail or rail 17 to receive the radiation beams of the radiation apparatuses 11*a*, 11*b* and 11*c* at different positions opposite to the radiation apparatuses 11*a*, 11*b* and 11*c*. There are many ways to realize the movement of the detector, which is not limited in the present disclosure, and only the above is used as an example for illustration.

The foregoing descriptions are merely embodiments of the present disclosure, and do not limit the scope of the present disclosure. Any equivalent structure or equivalent process transformation using the description of the present disclosure and the accompanying drawings are directly or indirectly applied to other related technologies shall fall within the protection scope of the present disclosure.

What is claimed is:

1. A radiotherapy equipment, comprising at least two radiation apparatuses wherein the radiation apparatuses are configured to be capable of emitting radiation beams that intersect at an intersection point for irradiation treatment of a target region, the radiation apparatuses are rotatable circumferentially about a rotation axis, radiation beams emitted by each of the radiation apparatuses when rotating circumferentially about the rotation axis form one rotating surface, and radiation positions of at least two of the radiation apparatuses are fixedly positioned at different cross-sections with respect to the rotation axis such that rotating surfaces formed by radiation beams emitted by the at least two of the radiation apparatuses when rotating circumferentially about the rotation axis do not coincide with each other, wherein the different cross-sections are sections passing through different positions of the rotation axis and perpendicular to the rotation axis;

wherein the radiotherapy equipment further comprises at least one detector panel, and the at least one detector panel is arranged at an opposite side of the radiation apparatuses and is configured to receive the radiation beams of the radiation apparatuses to detect dosages or field shapes of the radiation beams of the radiation apparatuses.

2. The radiotherapy equipment according to claim 1, wherein the intersection point is on the rotation axis.

3. The radiotherapy equipment according to claim 1, wherein the radiation position of at least one of the radiation apparatuses is positioned at a cross-section where the intersection point is located.

4. The radiotherapy equipment according to claim 1, wherein the radiation position of at least one of the radiation apparatuses is not positioned at a cross-section where the intersection point is located, and the angle between the cross-section where the intersection point is located and the connecting line between the intersection point and the radiation position of the radiation apparatuses is 0° to 60°.

5. The radiotherapy equipment according to claim 1, wherein each of the radiation apparatuses is provided with a rotating device, and the rotating device drives the corresponding radiation apparatus to rotate circumferentially about the rotation axis; or, at least two of the radiation apparatuses are arranged on a rotating device, and the rotating device drives the at least two of the radiation apparatuses to rotate circumferentially about the rotation axis.

6. The radiotherapy equipment according to claim 5, wherein the rotating device is a manipulator or a gantry.

7. The radiotherapy equipment according to claim 1, wherein the radiation apparatuses are X-ray generators; or, the radiation apparatuses are γ-ray devices; or, the radiation apparatuses comprise an X-ray generator and a γ-ray device.

8. The radiotherapy equipment according to claim 7, wherein the radiotherapy equipment comprises three of the radiation apparatuses, and the three radiation apparatuses are all X-ray generators.

9. The radiotherapy equipment according to claim 8, wherein the radiation positions of the three radiation apparatuses are positioned at different cross-sections; or, the radiation positions of two of the radiation apparatuses are positioned at the same cross-section, and the radiation positions of the two of the radiation apparatuses and the radiation position of the third radiation apparatus is positioned at a different cross-section.

10. The radiotherapy equipment according to claim 1, wherein each of the radiation apparatuses is provided with a collimator, the collimator provides a radiation beam channel for shaping radiation beams, and the collimators of the radiation apparatuses are of different types.

11. The radiotherapy equipment according to claim 10, wherein the collimator is provided with a plurality of radiation beam channels having different aperture sizes; or, the collimator is able to shape radiation beam channels of different sizes and/or shapes.

12. The radiotherapy equipment according to claim 1, wherein the radiotherapy equipment further comprises an imaging device, and the imaging device comprises a beam generator and a beam receiving detector.

13. The radiotherapy equipment according to claim 1, wherein the detector panel is capable of receiving the radiation beams of at least two of the radiation apparatuses; or, the detector panel is capable of receiving the radiation beams of the radiation apparatuses and the beam generator.

14. A radiotherapy equipment, comprising at least two radiation apparatuses, wherein the radiation apparatuses are configured to capable of emitting radiation beams that intersect at a target region for irradiation treatment of the target region, the radiation apparatuses are rotatable circumferentially about a rotation axis, radiation beams emitted by each of the radiation apparatuses when rotating circumferentially about the rotation axis form one rotating surface, and at least two of the radiation apparatuses are fixedly positioned at different axial positions with respect to the rotation axis such that rotating surfaces formed by radiation beams emitted by the at least two of the radiation apparatuses when rotating circumferentially about the rotation axis do not coincide with each other, wherein the different cross-sections are sections passing through different positions of the rotation axis and perpendicular to the rotation axis;

wherein the radiotherapy equipment further comprises at least one detector panel, and the at least one detector panel is arranged on an opposite side of the radiation apparatuses and is configured to receive the radiation beams of the radiation apparatuses to detect dosages or field shapes of the radiation beams of the radiation apparatuses.

15. The radiotherapy equipment according to claim 14, wherein the radiation apparatuses are X-ray generators; or, the radiation apparatuses are γ-ray devices; or, the radiation apparatuses comprise an X-ray generator and a γ-ray device.

16. A radiotherapy equipment, comprising at least two radiation apparatuses, wherein the radiation apparatuses are configured to capable of emitting radiation beams that intersect at a target region for irradiation treatment of the target region, radiation beams emitted by each of the radiation apparatuses when rotating circumferentially about a rotation axis form one rotating surface, and at least two of the radiation apparatuses are fixedly positioned at different axial positions with respect to the rotation axis such that rotating surfaces formed by radiation beams emitted by the at least two of the radiation apparatuses when rotating circumferentially about the rotation axis do not coincide with each other, wherein the different cross-sections are sections passing through different positions of the rotation axis and perpendicular to the rotation axis;

wherein the radiotherapy equipment further comprises at least one detector panel, and the at least one detector panel is arranged on an opposite side of the radiation apparatuses and is configured to receive the radiation beams of the radiation apparatuses to detect dosages or field shapes of the radiation beams of the radiation apparatuses.

17. The radiotherapy equipment according to claim 1, wherein the radiotherapy equipment comprises at least three radiation apparatuses, the radiation position of at least one of the at least three radiation apparatuses is positioned at the cross-section where the intersection point is located, the radiation position of at least one of the at least three radiation apparatuses is positioned such that a connecting line between the intersection point and the radiation position forms a first angle with the cross-section where the intersection point is located, and the radiation position of at least one of the at least three radiation apparatuses is positioned such that a connecting line between the intersection point and the radiation position forms a second angle with the cross-section where the intersection point is located, so that rotating surfaces formed by radiation beams emitted by the at least three apparatuses when rotating circumferentially about the rotation axis do not coincide with each other, wherein the first angle is different from the second angle, and the first angle and the second angle are in the range of 0° to 60°.

* * * * *